United States Patent [19]

Lumm

[11] Patent Number: 5,127,756
[45] Date of Patent: Jul. 7, 1992

[54] MULTI-COMPARTMENT DEVICE FOR MEDICAL APPLICATIONS

[76] Inventor: Caroline V. Lumm, P.O. Box 321, McClure, Ohio 43534

[21] Appl. No.: 665,008

[22] Filed: Mar. 5, 1991

[51] Int. Cl.$^5$ .............................................. B42F 13/00
[52] U.S. Cl. ..................................... 402/79; 283/900; 402/500
[58] Field of Search ................... 402/79, 500; 283/900

[56] References Cited

U.S. PATENT DOCUMENTS 4,244,660 1/1981 Aronson ......................... 402/500 X

FOREIGN PATENT DOCUMENTS 2380889 10/1978 France ............................... 402/500

OTHER PUBLICATIONS

Pages M288-M302, Sea Gate Office Products 1991 Catalog.
Pages 6 and 7, 1990 Catalog of Carstens Health Industries, Inc.
1991 General Catalog-patient Charting Equipment and Supplies of First Hospital Products, Inc.

Primary Examiner—Paul A. Bell
Attorney, Agent, or Firm—MacMillan, Sobanski & Todd

[57] ABSTRACT

A multi-compartment device which is placed in a binder to organize and schedule a patients medical requirements. The device is constructed from a sheet of transparent vinyl material. The sheet includes one or more first compartments located in the center of the sheet for holding, for example, a picture of the patient and any other desired information. A second plurality of compartments are provided along an outer edge of the sheet for holding a patient name tag. Finally, the sheet includes a third plurality of compartments provided on an upper and/or lower edge thereof. Each third compartment holds a correspondingly shaped member which is moveable upwardly and downwardly within the compartment. In one position for each member, an end portion of the member is hidden within the compartment. When the member is moved to the other position within the compartment, the end portion thereof extends beyond the edge of the sheet. The two different positions of each member can be used to indicate different medical or service requirements.

10 Claims, 1 Drawing Sheet

MULTI-COMPARTMENT DEVICE FOR MEDICAL APPLICATIONS

TECHNICAL FIELD

This invention relates in general to information storing devices and in particular to a multi-compartment device for placement in a three ring binder to organize and schedule a person's medical requirements and to eliminate the possibility of error of ommission.

BACKGROUND ART

A typical nursing home is a very busy place having two to three shifts of staff working during a given twenty four hour period. Each shift is required to provide a number of different services to a patient including the administering of medication which is prescribed for the patient. It is imperative that such medication be given at regular intervals in order that the medication levels are sustained. One patient may, for example, take one medication once per day, another every 4 hours and a third every 6 hours. During the change of a shift there may be miscommunication between a nurse coming on duty from a nurse completing duty regarding what medicines were given, when they were given and what medicines were not given. Further, a great number of patients in the nursing home are not in full capacity of their mental faculties, preventing the nurse from asking the patient if they have been given their medicine. As a result, a patient may not be given medication at the correct time or is given a double dose if it is not clear that the patient received the medicine from the shift just completed. Thus, it is desirable to have a simple and inexpensive device which will tell a nurse if a specific patient has been given medication and if so, the time of the next dose.

DISCLOSURE OF THE INVENTION

The invention is directed to a multi-compartment device which is placed in a patient binder to organize/and to schedule the patients medicine and or service requirements. The device is preferably constructed from a sheet of clear plastic material, such as vinyl. The sheet is perforated along an inner edge for insertion into the binder. One or more first compartments are provided in the center of the sheet. These compartments are for holding a picture of the patient and/or any other vital information which is desired. A plurality of second compartments are provided along an outer edge of the sheet. These compartments are for holding a name tag of the particular patient. The name tags in successive sheets in the binder can be staggered alphabetically or by room and bed location by placing the name tag in the appropriate second compartment on each particular sheet. The sheet also includes a plurality of third compartments along an upper or lower edge of the sheet. The third compartments are designed for holding correspondingly shaped members which are individually moveable upwardly and downwardly within the compartments. Preferably, the different members in the third compartments of a sheet are of different colors.

When the third compartments are along the lower edge and a member is in the upward direction, an end portion of the member is hidden within the compartment. However, when the member is moved downwardly within the compartment, the end portion thereof extends beyond a bottom edge of the sheet. The two different positions of the member can indicate any number of different medical requirements. For example, to indicate to the nurse that a medication has been given, the member would have been pushed to the upward position. Conversely, if the nurse is to administer a medication to a patient, a member on the patient's sheet can be left in the downward position. More than one member can be used and/or the members can be color coded and organized to indicate specific requirements, such as the times that medications or services are to be administered. At the beginning of a shift, the nurse flags all medicines and treatment and other pertinent information needed for each patient for the entire shift.

It is an object of the invention to provide a multi-compartment device for placement in a binder to organize and schedule requirements and which is simple and inexpensive in construction and operation.

Other objects and advantages of the invention will become apparent to those skilled in the art from the following detailed description of a preferred embodiment of the invention, in connection with the accompanying drawings.

BEST MODE FOR CARRYING OUT THE INVENTION

Figure 1:
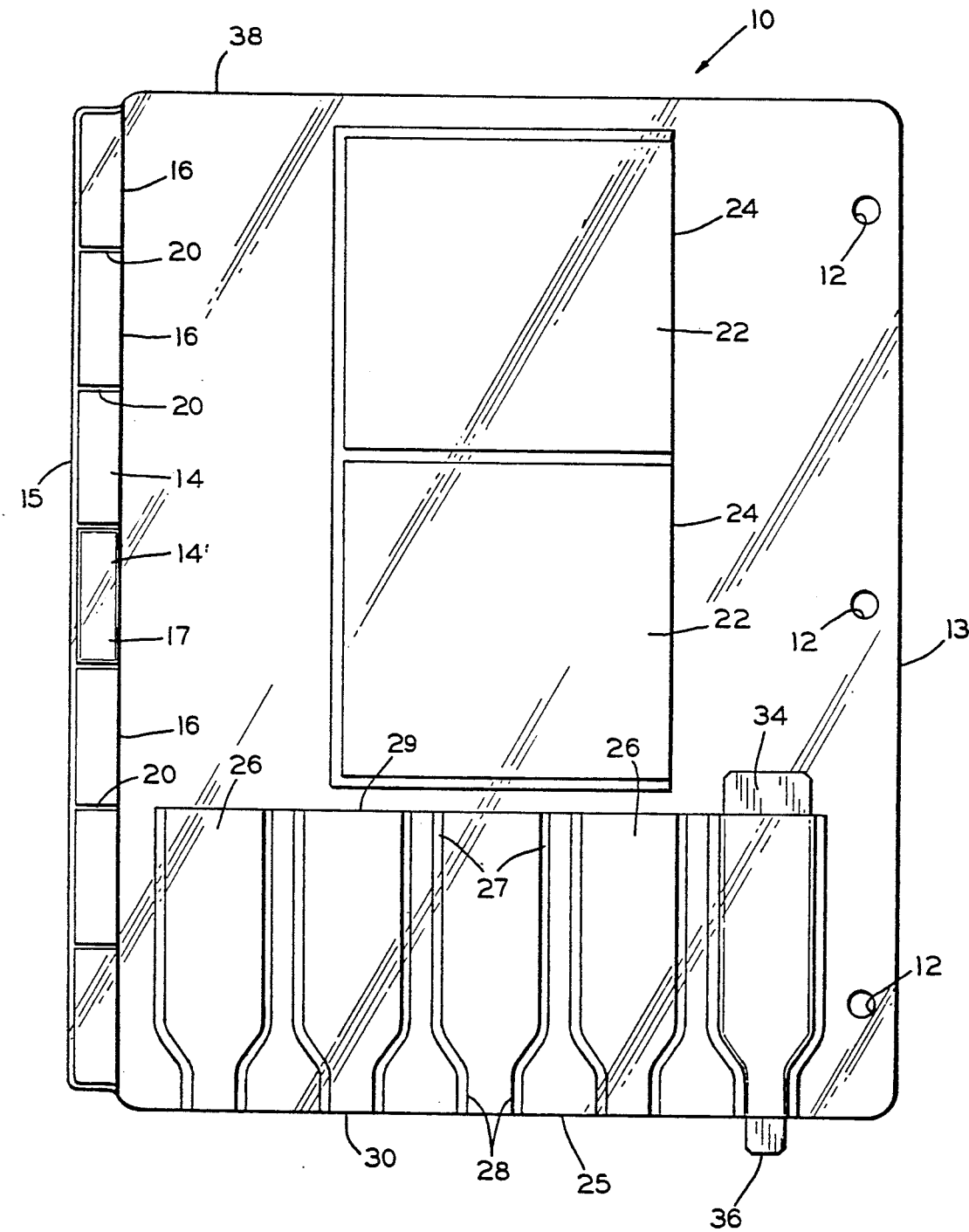
FIG. 1 is a plan view of a multi-compartment device which can be secured within a three ring binder to organize and schedule a patient's medical requirements, constructed in accordance with this invention.

Referring to the drawings, FIG. 1 illustrates a multi-compartment notebook sheet 10, constructed in accordance with the invention. The sheet 10 is preferably constructed from a stiff flexible clear plastic material, such as vinyl, and may be sized, for example, approximately eight and one-half inches wide by eleven inches long. This particular size allows the sheet 10 to be placed within a standard binder (not shown).

The sheet 10 is shown with three openings 12 formed along an inner edge 13 thereof. The number and spacing of the openings 12 are designed to be received by a binder (not shown) for holding the sheets 10. An opposite outer edge 15 of the sheet 10 has a longitudinal row of open compartments 14 formed therealong. Each of the compartments 14 has an open edge 16 adapted to receive a name tag 17, shown in one compartment 141. Seven individual compartments 14 are shown. However, this number can be varied to meet a users particular requirements for the sheet 10. The compartments 14 are constructed out of the same material as the sheet 10. The compartments 14 can be formed by placing the sheet of the compartment material on the sheet 10 and securing the sheets together along the edge 15. The sheets can be secured along a seam, for example, by known heat sealing or ultrasonic welding technique. When the compartment material is secured to the sheet 10 seams 20 are formed to separate the individual compartments 14.

The sheet 10 further includes one or more compartments 22 (two illustrated) which are generally rectangular in shape. The compartments 22 may be constructed out of the same material as the sheet 10 and are formed by known techniques. One edge 24 of each compartment 22 is left open to receive an article (not shown).

A row of transversely extending compartments 26 is shown along a lower edge 25 of the sheet 10. The compartments 26 preferably have parallel edge portions 27 with a predetermined spacing. Such spacing is reduced at edge portions 28 adjacent the sheet edge 25. Each compartment 26 has an open upper end 29 and an open lower end 30. The lower end 30 is flush with the lower edge 25 of the sheet 10. The compartments 26 may be constructed out of the same material as the sheet 10.

The completed multi-compartment sheet 10 may be used in nursing home applications in the following manner. A picture (not shown), of a patient is slipped within one of the compartments 22 in order to identify the patient. Any other compartments 22 can hold any special information regarding the patient which is desired. Such information can include drug administration orders, a list of drugs which trigger an allergic reaction, or telephone numbers of family members to contact in the event of an emergency.

One of the side compartments 14 can receive a patient's name tag to provide a quick reference to identify a patient. Seven compartments 14 are provided on each sheet 10 to allow the name tags to be staggered when a plurality of sheets 10 are placed in the notebook binder. Thus, up to seven names can be seen at one time in the binder without having to turn a single sheet 10. Preferably, the sheets 10 are arranged in the binder in a sequence corresponding to the location of the patients.

The bottom compartments 26 are adapted to receive a correspondingly shaped member 34 therein. Although only a single member 34 is illustrated, a separate member 34 will be placed in each compartment 26 and each member preferably has a different color. Each member 34 is moveable upwardly and downwardly within the compartment 26 to have an end portion 36 which can extend below the lower edge 25 of the sheet 10 when the member 34 is in the downward position. Each member 34 is retained in a compartment 26 by the narrow spacing between the compartment side portions 28, while allowing the end portion 36 to extend from the compartment 26. The downward position for a particular color and the location of a member 34 can indicate to a nurse that a patient needs to be given medication or provided other service at a particular time. Once the medication or service is given, the member 34 can be pushed upwardly until the end portion 36 is totally within the compartment 26. Thus, by simply moving the member 34 between these two positions, a nurse will readily know if a patient has received a needed medication or service. Furthermore, a plurality of such members 34 can be utilized and can be color coded to indicate a specific time which a medication or service is to be given. The illustrated sheet 10 allows five different members 34 to be inserted into the compartments 26 providing up to five different times at which a medicine or service is to be given. Thus, the invention provides a simple and inexpensive way of keeping track of a patient's medication or other requirements along with organizing other vital information pertaining to the person.

Although the device has been shown and described for use in a three ring binder and in nursing home applications, it is anticipated that the device may be adapted to fit other types of binders and that the device can be used in a hospital or in any other environment where it is necessary to give medications or to provide services at different times. Furthermore, it is anticipated that the number, shape and arrangement of the individual compartments can be varied in order to accommodate the particular use of the device. The location of the compartments 26 may be changed to meet the users needs. For example, the compartments 26 may be located along an upper edge 38 of the sheet 10 rather than along the lower edge 25. Or, the compartment 26 can be located along both the lower edge 25 and the upper edge 38. Further, the number of compartments 14 and 22 may be changed to meet a users needs. Although the sheet 10 is preferably formed of a transparent material, it will be appreciated that only one side of the compartments 14 and 22 used be formed from a transparent material to render contents visible. Various other modifications and changes may be made to the sheet 10 without departing from the spirit and the scope of the following claims.

I claim:

1. A device for placement in a binder comprising a generally rectangular sheet of material having first, second, third and fourth edges, means adjacent said first edge for securing said sheet in the binder, a plurality of first compartments formed on said sheet to be spaced along said second edge, a separate member located in each first compartment, each member having first and second end portions and being moveable between a first position wherein said second end portion is within the compartment and a second position wherein said second end portion projects from the compartment past said second edge, a plurality of transparent second compartments spaced along said third edge, each second compartment having a closed edge at said third edge and an open edge directed away from said third edge, said second compartments selectively receiving an identifier tag, whereby identifier tags on devices in the binder may be staggered for viewing through adjacent devices.

2. The device of claim 1, and further including at least one third compartment spaced from said first, second and third edges, said third compartment having a transparent side to facilitate viewing the contents of said third compartment.

3. The device of claim 1, and wherein said first compartments each have a maximum width and an opening of a lesser width adjacent said second edge, wherein each member first end portion is of a width greater than said lesser width and each member second end portion is of a width less than said lesser width, and wherein said second end portion of a member projects from a compartment opening when in said second position.

4. A device for indicating when a patient needs attending to comprising a flat sheet of material, said sheet having a plurality of first compartments adjacent a first edge thereof, each of said first compartments having a predetermined maximum width and an opening adjacent said first edge of a width less than said predetermined maximum width, a separate member inserted into each of said first compartments and moveable in said first compartments between a first position and a second position, each of said members having a portion having a width greater than said opening width and having an end portion of a width no greater than said opening width, said end portion on a member projecting from said first edge when such member is in said first position and being retracted into a first compartment when such member is in said second position, each of said members indicating a patient's needs when in said first position.

5. The device according to claim 4, and wherein said sheet is constructed from a transparent vinyl material.

6. The device according to claim 1, and wherein said first compartments are formed from a second flat sheet of material welded to the first sheet.

7. The device according to claim 4, and further including a plurality of transparent second compartments spaced along a second edge of said sheet for receiving a patient identifier, said second compartments permitting staggering patient identifiers to facilitate reading when said sheets are stacked.

8. The device according to claim 7, and further including at least one transparent third compartment on said sheet adjacent a middle portion of said sheet.

9. The device according to claim 8, and wherein said sheet has a binder edge opposite said second edge, and a plurality of apertures formed in said sheet adjacent said binder edge, said apertures being spaced to be received by a binder.

10. The device of claim 4, and wherein said members are of different colors to indicate different patient needs.

* * * * *